US00PP17849P2

(12) United States Plant Patent
Wilson

(10) Patent No.: US PP17,849 P2
(45) Date of Patent: Jul. 3, 2007

(54) ***DIGITALIS* PLANT NAMED 'SPICE ISLAND'**

(50) Latin Name: *(Digitalis lanata×grandiflora)×(Digitalis laevigata)*
Varietal Denomination: Spice Island

(76) Inventor: Heather Wilson, Spindrift, The Ridge, Bussage, Stroud, Gloucestershire GL6 8BB (GB)

( * ) Notice: Subject to any disclaimer, the term of this patent is extended or adjusted under 35 U.S.C. 154(b) by 184 days.

(21) Appl. No.: 11/141,345

(22) Filed: May 31, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Digitalis* plant named 'Spice Island', characterized by its upright and sturdy plant habit; short internodes; dense and bushy plant form; long flower racemes; freely flowering habit; and orange and yellow-colored flowers.

1 Drawing Sheet

Botanical designation: (*Digitalis lanata×grandiflora*)×(*Digitalis laevigata*).
Cultivar denomination: 'Spice Island'.

BACKGROUND OF THE INVENTION

The present Invention relates to a new and distinct cultivar of *Digitalis* plant, botanically known as (*Digitalis lanata×grandiflora*)×(*Digitalis laevigata*), and hereinafter referred to by the cultivar name 'Spice Island'.

The new *Digitalis* is a product of a planned breeding program conducted by the Inventor in Stroud, Gloucestershire, United Kingdom. The objective of the breeding program was to create sturdy new *Digitalis* cultivers with numerous flowers with attractive coloration.

The new *Digitalis* originated from a cross-pollination made by the Inventor in 1995 of the *Digitalis lanata×Digitalis grandiflora* cultivar John Innes Tetra, not patented, as the female, or seed, parent with an unnamed selection of *Digitalis laevigata,* not patented, as the male, or pollen, parent. The new *Digitalis* was discovered and selected by the Inventor in August, 1998 as a single flowering plant within the progeny of the stated cross-pollination in a controlled environment in Stroud, Gloucestershire, United Kingdom.

Asexual reproduction of the new cultivar by tissue culture since 1999 in Stroud, Gloucestershire, United Kingdom has shown that the unique features of this new *Digitalis* are stable and reproduced true to type in successive generations.

SUMMARY OF THE INVENTION

Plants of the cultivar Spice Island have not been observed under all possible environmental conditions. The phenotype may vary somewhat with variations in environment such as temperature and light intensity without, however, any variance in genotype.

The following traits have been repeatedly observed and are determined to be the unique characteristics of 'Spice Island'. These characteristics in combination distinguish 'Spice Island' as a new and distinct *Digitalis* cultivar:

1. Upright and sturdy plant habit.
2. Short internodes; dense and bushy plant form.
3. Long flower racemes with numerous closely-spaced flowers.
4. Orange and yellow-colored flowers.

Plants of the new *Digitalis* can be compared to the female parent, the cultivar John Innes Tetra. Compared to plants of the cultivar John Innes Tetra, plants of the new *Digitalis* are taller, have shorter internodes and flowers are more closely spaced on the racemes.

Plants of the new *Digitalis* can be compared to the male parent, the unnamed selection of *Digitalis laevigata.* Compared to flowers of plants of the male parent, flowers of plants of the new *Digitalis* are more closely spaced on the racemes and are richer in color.

Plants of the new *Digitalis* can be compared to plants of the *Digitalis* cultivar Carillon, not patented. Plants of the new *Digitalis* differ primarily from plants of the cultivar Carillon in flower color. In addition, flowers of plants of the new *Digitalis* are more closely spaced together than flowers of plants of the cultivar Carillon.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Digitalis.*

The photograph at the left of the sheet comprises a side perspective view of typical flowering plants of 'Spice Island' grown in an outdoor nursery.

The photograph at the right of the sheet is a close-up view of a typical flower raceme of 'Spice Island'.

DETAILED BOTANICAL DESCRIPTION

Plants shown in the aforementioned photographs and used in the following description were grown under conditions which closely approximate commercial production conditions during the late spring in an outdoor nursery in Stroud, Gloucestershire, United Kingdom. Plants were about two years old when the photographs and description were taken. In the following description, color references are made to The Royal Horticultural Society Colour Chart, 1995 Edition, except where general terms of ordinary dictionary significance are used.

Botanical classification: (*Digitalis lanata*×*grandiflora*)× (*Digitalis laevigata*) cultivar Spice Island.

Parentage:

*Female, or seed, parent.*—*Digitalis lanata*×*grandiflora* cultivar John Innes Tetra, not patented.

*Male, or pollen, parent.*—Unnamed selection of *Digitalis laevigata,* not patented.

Propagation:

*Type.*—By tissue culture.

*Root description.*—Fine; freely branching.

Plant description:

*Form.*—Perennial. Upright and sturdy plant habit; narrow inverted triangle. Freely basal branching with about two to five flowering stems per plant; dense and bushy plant habit; moderately vigorous growth habit. Numerous flowers arranged on crowded terminal racemes.

*Plant height.*—About 80 cm.

*Plant width.*—About 30 cm.

*Lateral stem description.*—Length (excluding inflorescence): About 50 cm. Diameter: About 1.5 cm. Internode length: About 1.5 to 2.5 cm. Strength: Strong. Aspect: Erect. Texture: Smooth, glabrous. Color: 144C; towards the base, overlain with 187A.

*Foliage description.*—Arrangement: Alternate, simple. Quantity per stem: About 45. Length: About 14 to 20 cm. Width: About 3 to 4 cm. Shape: Lanceolate. Apex: Apiculate. Base: Cuneate. Margin: Serrate. Texture, upper and lower surfaces: Smooth, glabrous; margins, pubescent. Venation pattern: Pinnate. Color: Developing foliage, upper surface: Closest to 137B. Developing foliage, lower surface: Closest to 147B. Fully expanded foliage, upper surface: Closest to 137B; towards the apex, 187A. Fully expanded foliage, lower surface: Between 146B and 147B. Venation, upper surface: 146C. Venation, lower surface: 146D. Petiole length: About 30 cm. Petiole diameter: About 1 cm. Petiole texture, upper and lower surfaces: Slightly pubescent. Petiole color, upper and lower surfaces: 144C.

Flower description:

*Flower arrangement and shape.*—Single bilabiate campanulate flowers closely spaced, about 1.5 cm apart, on upright terminal racemes; flowers face mostly outward. Freely flowering habit, about 60 flowers per raceme.

*Natural flowering season.*—Continuous flowering during the summer (June through July) in the United Kingdom.

*Flower longevity on the plant.*—Individual flowers last about ten days on the plant. Flowers not persistent.

*Flower buds.*—Length: About 1 cm. Diameter: About 5 mm. Shape: Ovoid. Color: 146A.

*Inflorescence size.*—Length: About 35 cm. Diameter: About 8 cm.

*Flowers.*—Diameter: About 1.8 cm. Depth (height): About 3.8 cm.

*Petals.*—Arrangement: Bilabiate and campanulate; four upper petals fused towards the base; one lower lip petal. Length, upper petals: About 2.5 cm. Length, lower lip petal: About 3.8 cm. Width, upper petals: About 8 mm. Width, lower lip petal: About 1.6 cm. Shape: Ovate. Apex: Cuspidate. Margin: Entire. Texture, upper and lower surfaces: Smooth, velvety. Color, upper petals: When opening, upper surface: 145C blushed with about 181A. When opening, lower surface: 144C blushed with about 181A. Fully opened, upper surface: 163A to 163B; venation close to 163A. Fully opened, lower surface: 163B; venation about 181A fading to 163A. Color, lateral petals: When opening, upper surface: 145C blushed with 163C. When opening, lower surface: 144C. Fully opened, upper surface: 163C; venation close to 163A. Fully opened, lower surface: 163B; venation about 181A fading to 163A. Color, lower lip petal: When opening, upper and lower surfaces: 145C; venation, 181A. Fully opened, upper surface: 162D to 163B; venation, about 181A fading to 163A. Fully opened, lower surface: 162C; venation close to 163A.

*Sepals.*—Arrangement/quantity per flower: Five, not fused. Length: About 1.5 cm. Width: About 3 mm. Shape: Lanceolate. Apex: Acute. Base: Cuneate. Margin: Entire. Texture, upper and lower surfaces: Pubescent. Color, upper and lower surfaces: 137C.

*Peduncles.*—Length: About 34 cm. Diameter: About 7 mm. Aspect: Erect. Strength: Strong. Flowers not fragrant. Color: 144A.

*Pedicels.*—Length: About 5 mm. Diameter: About 1 mm to 2 mm. Aspect: Mostly erect. Strength: Strong. Color: 137C.

*Reproductive organs.*—Stamens: Quantity per flower: Four. Filament length: About 1 cm. Filament color: 10D. Anther shape: Reniform. Anther length: About 3 mm. Anther color: 10B. Pollen amount: Moderate Pollen color: 11D. Pistils: Quantity per flower: One. Pistil length: About 2 cm. Stigma color: 144B. Style length: About 1.2 cm. Style color: 145C. Ovary color: 144A.

*Fruit/seeds.*—Fruit and seed development have not been observed on plants of the new *Digitalis.*

Disease/pest resistance: Plants of the new *Digitalis* have not been noted to be resistant to pathogens and pests common to *Digitalis.*

High temperature tolerance: Plants of the new *Digitalis* have been observed to tolerate temperatures up to 28° C.

Hardiness: Plants of the new *Digitalis* have been observed to be hardy to about −6° C.

It is claimed:

1. A new and distinct cultivar of *Digitalis* plant named 'Spice Island', as illustrated and described.

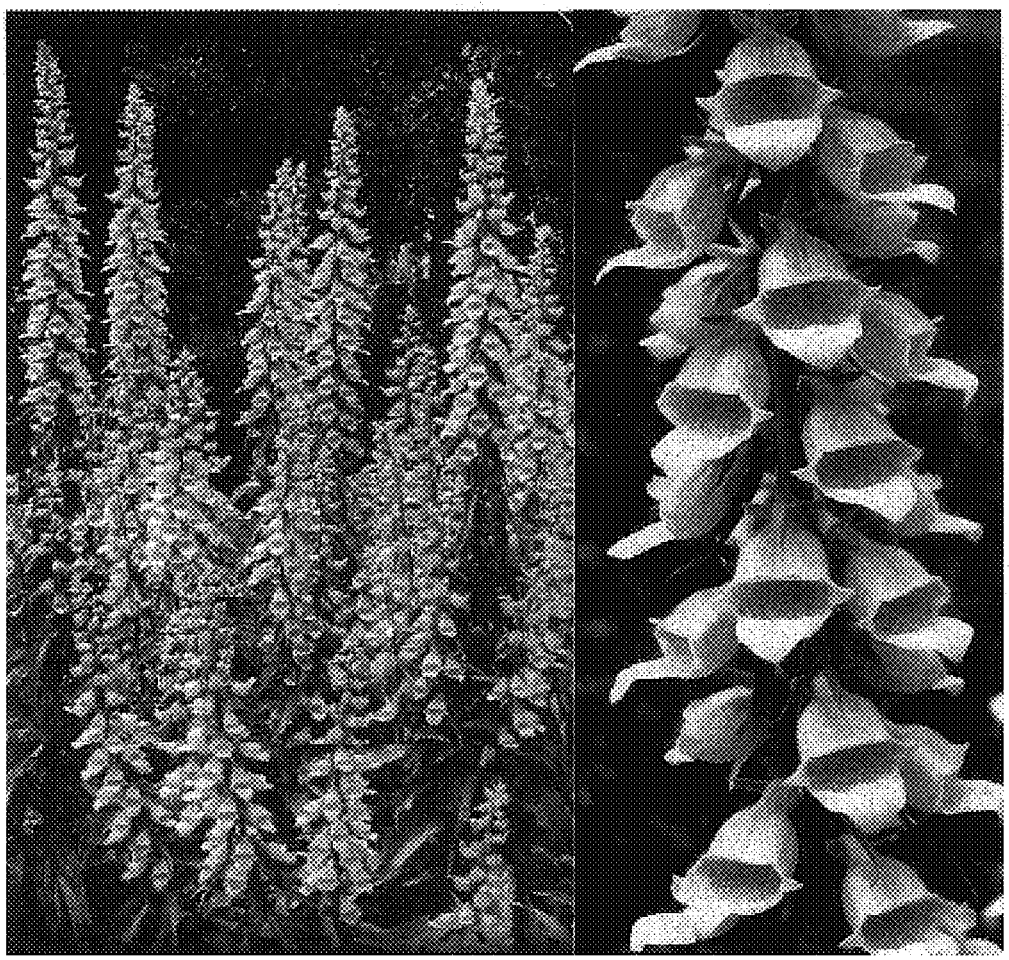

* * * * *